(12) United States Patent
Kato

(10) Patent No.: US 10,946,181 B2
(45) Date of Patent: Mar. 16, 2021

(54) TRANSDERMAL ADMINISTRATION DEVICE

(71) Applicant: TOPPAN PRINTING CO., LTD., Tokyo (JP)

(72) Inventor: Hiroyuki Kato, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 255 days.

(21) Appl. No.: 16/102,427

(22) Filed: Aug. 13, 2018

(65) Prior Publication Data

US 2018/0345000 A1    Dec. 6, 2018

Related U.S. Application Data

(63) Continuation of application No. PCT/JP2017/012152, filed on Mar. 24, 2017.

(30) Foreign Application Priority Data

Mar. 25, 2016  (JP) .............................. JP2016-062420

(51) Int. Cl.
*A61M 37/00* (2006.01)
*A61K 9/00* (2006.01)

(52) U.S. Cl.
CPC ....... *A61M 37/0015* (2013.01); *A61K 9/0021* (2013.01); *A61K 9/0014* (2013.01);
(Continued)

(58) Field of Classification Search
CPC .... A61M 2037/0038; A61M 2037/003; A61M 2037/0023; A61M 2037/0046;
(Continued)

(56) References Cited

U.S. PATENT DOCUMENTS

| 8,491,534 B2* | 7/2013 | Takada | A61K 9/0021 |
| | | | 604/173 |
| 9,539,418 B2* | 1/2017 | Quan | A61Q 19/08 |

(Continued)

FOREIGN PATENT DOCUMENTS

| EP | 2 578 264 A1 | 4/2013 |
| EP | 2 633 881 A1 | 9/2013 |

(Continued)

OTHER PUBLICATIONS

International Search Report with English language translation and Written Opinion issued in International Application No. PCT/JP2017/012152 dated Jun. 27, 2017.

(Continued)

*Primary Examiner* — Laura A Bouchelle
(74) *Attorney, Agent, or Firm* — Foley & Lardner LLP

(57) ABSTRACT

A plurality of projections in a transdermal administration device each include a columnar portion extending from a first surface of a substrate, and a tapered portion extending from a top of the columnar portion. A maximum angle of an apex of the tapered portion viewed in a direction parallel with the first surface is in a range of 10° or more and 30° or less, a ratio of a length from a proximal end to a distal end of the tapered portion to a length from a proximal end to a distal end of the projection as viewed in a direction perpendicular to the first surface is in a range of 0.45 or more and 0.75 or less, and a pitch (distance between centers of closest projections), viewed in a direction perpendicular to the first surface is in a range of 50 μm or more and 350 μm or less.

9 Claims, 4 Drawing Sheets

(52) U.S. Cl.
CPC ............... *A61M 2037/0023* (2013.01); *A61M 2037/0046* (2013.01); *A61M 2037/0053* (2013.01); *A61M 2037/0061* (2013.01)

(58) Field of Classification Search
CPC .. A61M 2037/0053; A61M 2037/0061; A61M 37/00; A61M 37/0015
See application file for complete search history.

(56) References Cited

U.S. PATENT DOCUMENTS

| | | | |
|---|---|---|---|
| 2008/0208134 A1* | 8/2008 | Tomono | A61P 3/10 604/173 |
| 2011/0028905 A1* | 2/2011 | Takada | A61K 31/496 604/180 |
| 2013/0072874 A1 | 3/2013 | Tokumoto et al. | |
| 2013/0296790 A1* | 11/2013 | Masaoka | A61M 37/0015 604/173 |
| 2015/0030642 A1 | 1/2015 | Wu et al. | |
| 2016/0058992 A1* | 3/2016 | Chen | B29C 33/424 604/46 |
| 2019/0001109 A1* | 1/2019 | Kim | C08B 15/04 |

FOREIGN PATENT DOCUMENTS

| | | |
|---|---|---|
| EP | 3 398 645 A1 | 11/2018 |
| JP | 2010-029634 A | 2/2010 |
| JP | 2015-016160 A | 1/2015 |
| JP | 2017-071109 A | 4/2017 |
| WO | WO-2008/020633 A1 | 2/2008 |
| WO | WO-2015/016235 A1 | 2/2015 |

OTHER PUBLICATIONS

Extended European Search Report dated Mar. 4, 2019 in corresponding application No. 17770445.9.

* cited by examiner

TRANSDERMAL ADMINISTRATION DEVICE

CROSS-REFERENCE TO RELATED PATENT APPLICATIONS

This application is a continuation application filed under 35 U.S.C. § 111(a) claiming the benefit under 35 U.S.C. §§ 120 and 365(c) of International Patent Application No. PCT/JP2017/012152, filed on Mar. 24, 2017, which is based upon and claims the benefit of priority to Japanese Patent Application No. 2016-062420, filed on Mar. 25, 2016. The disclosures of which are all hereby incorporated herein by reference in their entireties.

TECHNICAL FIELD

The present invention relates to transdermal administration devices used for drug administration.

BACKGROUND ART

Transdermal administration devices are used for administration of a drug into an administration target through the skin. A microneedle, which is an example of the transdermal administration device, includes a plurality of needle-shaped projections and a plate-shaped substrate. The plurality of projections are arranged on the surface of the substrate. In administration of a drug, a user holds a microneedle with the distal ends of the projections oriented toward the skin and presses the substrate against the skin. As the projections puncture the skin, a drug is delivered into the skin through holes created by the projections. Because the projections are micro-sized, drug administration using a microneedle can reduce pain which may occur during puncture of the skin (for example, see PTL 1).

CITATION LIST

[Patent Literature] PTL 1: JP 2015-016160 A

SUMMARY OF THE INVENTION

Technical Problem

For accurate drug administration, it is desired that a plurality of projections are sufficiently inserted into the skin to create holes of a desired depth suitable for the drug administration. For this reason, the projections are required to not be deformed by the pressing force applied through the substrate and to be inserted into the skin, penetrating the stratum corneum, which is the outermost layer of the skin, to reach a desired depth.

One of the elements that affects the puncture performance of the projections, that is, resistance to deformation and smooth puncture into the skin, is the shape of the projections. For example, projections having a sharper distal end more smoothly puncture the skin. However, the projection tends to have a lower strength and becomes more susceptible to deformation with an increase in sharpness of the distal end. Further, in a microneedle having a plurality of projections, a pressing force applied to the projections varies depending on the positions of the projections on the substrate. Accordingly, the arrangement of the plurality of projections also affects the degree of resistance to deformation of the respective projections.

Thus, the puncture performance of projections is affected by a plurality of elements, including an element that improves one of two requirements of the projections, i.e., resistance to deformation of the projections and smooth puncture into the skin, while being compromised by the other. Therefore, it is desired to examine the effects imparted by these elements on the puncture performance of the projections, and to determine conditions that can enhance both of the two requirements for the respective projections.

The present invention has an object of providing a transdermal administration device that can enhance puncture performance of the respective projections.

Solution to Problem

A transdermal administration device which attempts to improve and even solves the above problem includes a substrate having a first surface, and a plurality of projections extending from the first surface, each projection including a columnar portion having a columnar shape extending from the first surface and a tapered portion having a tapered shape extending from a top of the columnar portion, wherein, in each of the plurality of projections, a maximum angle of an apex of the tapered portion as viewed in a direction parallel with the first surface is in a range of 10° or more and 30° or less, a ratio of a taper length to a projection length is in a range of 0.45 or more and 0.75 or less, wherein the projection length is a length from a proximal end to a distal end of the projection in a direction perpendicular to the first surface, and the taper length is a length of from a proximal end to a distal end of the tapered portion in a direction perpendicular to the first surface, and a pitch, which is a distance between a center of one of the projections and a center of another projection closest to the one of the projections, is in a range of 50 μm or more and 350 μm or less, wherein the center of the projection is a center of gravity of a shape of outline of the projection as viewed in a direction perpendicular to the first surface.

According to the above configuration, the apexes of the projections are sufficiently sharp to allow smooth puncture into the skin by the projections. Because the projections have a shape composed of a columnar body and a tapered body connected thereto, the bottom of the projection is reduced in size compared with the projection having a configuration in which the entire projection has a tapered shape with the same tip angle. Accordingly, the pitch of the plurality of the projections can be reduced and thus the projections can be densely arranged. Because a pressing force applied to the substrate is distributed to thereby reduce the force applied to each projection, the projections can be prevented from being deformed during puncture while having sharp apexes. Moreover, because the proportion of the columnar portion in the projection does not become too large, the strength of the projection against a force in the direction parallel with the first surface can be prevented from decreasing even if the projections have a shape composed of a columnar body and a tapered body connected thereto. Thus, according to the above configuration, the projections can improve both resistance to deformation and smooth puncture into the skin, and thus improve puncture performance of the respective projections.

In the above configuration, the columnar portion may have a prism shape, and the tapered portion may have a pyramid shape. In the above configuration, the columnar portion may have a cylindrical shape, and the tapered portion may have a conical shape.

According to the above configuration, a projection having a shape composed of a columnar body and a tapered body connected thereto can be appropriately implemented. Further, among the shapes composed of a columnar body and a tapered body connected thereto, the shapes of the above configurations are simple with only a small change in curvature and relatively few corners, which allows for easy production of the projections.

In the above configuration, when viewed in the direction perpendicular to the first surface, the plurality of projections may be arrayed in a matrix with a pitch which is a distance between the centers of the adjacent projections in two directions perpendicular to each other on the first surface.

According to the configuration, because the respective projections are regularly arranged with an equal interval, a pressing force applied to the substrate is equally distributed. Accordingly, variation in puncture performance of the respective projections can be reduced.

In the above configuration, the projections are preferably made of a material containing a water-soluble polymer.

Generally, because the projection containing a water-soluble polymer as a main component is susceptible to deformation compared with the projection made of other materials such as metal, a problem that the projection has a difficulty in achieving both resistance to deformation and smooth puncture into the skin tends to appear. According to the above configuration, in the projections made of a material containing a water-soluble polymer, the projections can improve both resistance to deformation and smooth puncture into the skin, which is highly advantageous.

Desired Advantageous Effects of Invention

According to the present invention, the puncture performance of a plurality of projections included in a transdermal administration device can be improved.

DESCRIPTION OF REPRESENTATIVE EMBODIMENTS

Figure 1:
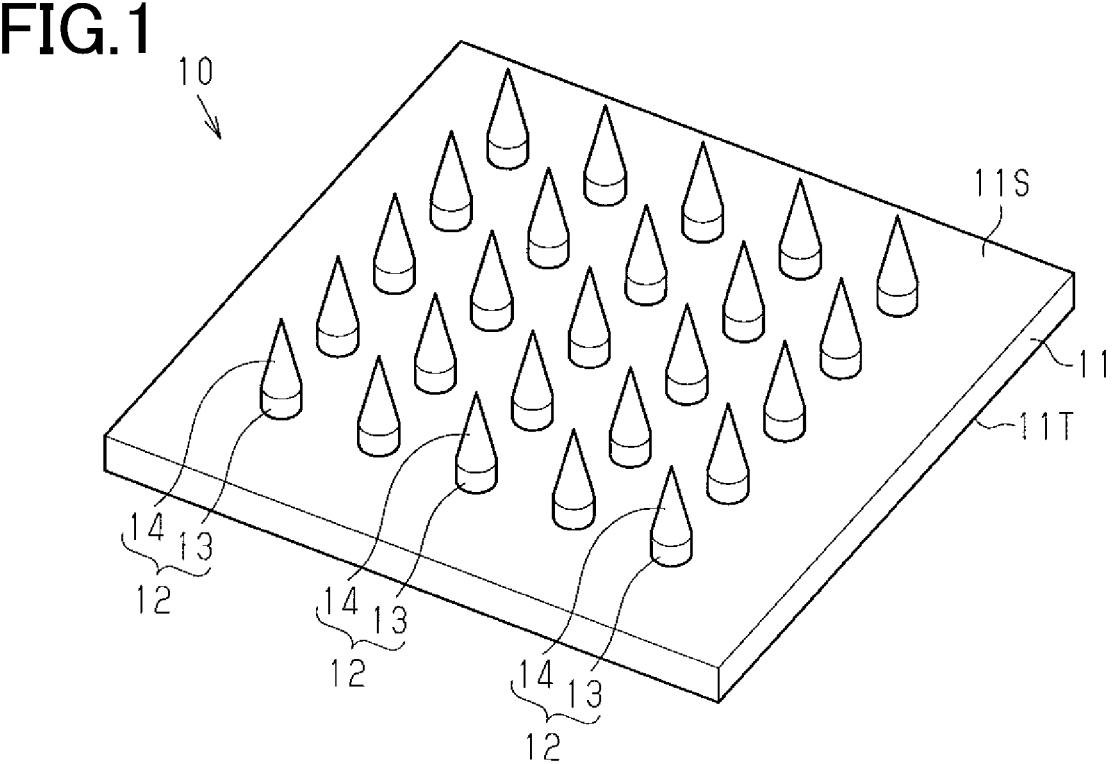
FIG. 1 is a perspective view which illustrates a perspective structure of a transdermal administration device according to an embodiment of the transdermal administration device.

With reference to FIGS. 1 to 5, an embodiment of a transdermal administration device will be described. With reference to these Figures, a preferred or representative embodiment of the present invention will be described in detail. It is to be understood that the present invention is not limited to the following embodiment, which are intended to be representative of the present invention. The representative embodiment described below is merely an example of the present invention, and the design thereof could be appropriately changed by one skilled in the art. In the embodiment, the same or corresponding components are denoted by the same reference characters, and duplicate description thereof will be omitted.

[Configuration of Transdermal Administration Device]

Figure 2:
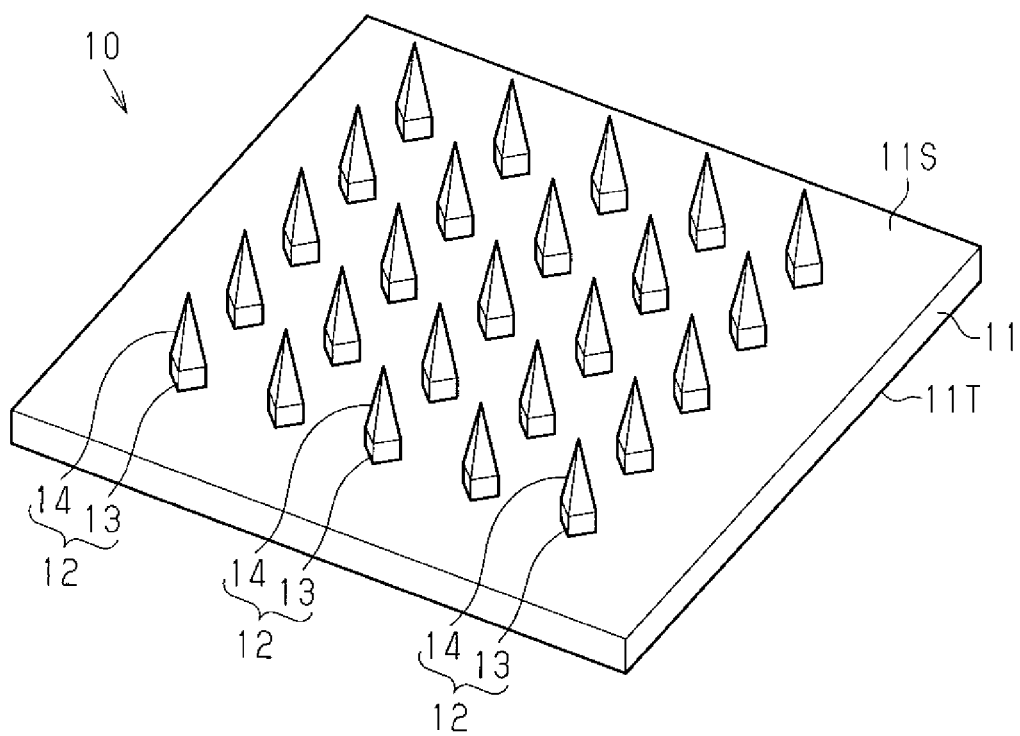
FIG. 2 is a perspective view which illustrates another example of a perspective structure of a transdermal administration device of an embodiment.

With reference to FIGS. 1 and 2, an overall configuration of a microneedle, which is an example of a transdermal administration device, will be described.

As shown in FIG. 1, a microneedle 10 includes a plate shaped substrate 11 and a plurality of projections 12 which protrudes from the substrate 11. The substrate 11 has a first surface 11S on which the projections 12 are disposed and a second surface 11T which is a surface opposite to the first surface 11S. The first surface 11S supports the proximal ends of the projections 12. That is, the plurality of projections 12 protrudes from the first surface 11S of the substrate 11. The outline of the substrate 11 as seen in the direction perpendicular to the first surface 11S is not specifically limited, and may be a circle, oval or rectangle.

The projection 12 is composed of a columnar portion 13 having a columnar shape extending from the first surface 11S and a tapered portion 14 having a tapered shape extending from the top of the columnar portion 13. In other words, the projection 12 has a shape in which the bottom of a tapered body is connected to the top of a columnar body.

Specifically, the columnar portion 13 has a side surface extending from the first surface 11S in the direction perpendicular to the first surface 11S. A cross-sectional area of the columnar portion 13 in the direction parallel with the first surface 11S is constant in the direction perpendicular to the first surface 11S.

The tapered portion 14 has a side surface extending from an upper end of the side surface of the columnar portion 13 toward a point located above the columnar portion 13. A cross-sectional area of the tapered portion 14 in the direction parallel with the first surface 11S gradually decreases as distance from the substrate 11. The cross-sectional shape of the tapered portion 14 in the direction parallel with the first surface 11S at every cross-section is preferably similar to the cross-sectional shape of the columnar portion 13 in the direction parallel with the first surface 11S.

The proximal end of the columnar portion 13 is the proximal end of the projection 12, and the distal end of the tapered portion 14 is the distal end of the projection 12. A bottom of the columnar portion 13 is the bottom of the projection 12, and is defined in the first surface 11S. The top of the columnar portion 13 corresponds to the bottom of the tapered portion 14, and is included in the projection 12. Further, the bottom and top of the columnar portion 13 and the bottom of the tapered portion 14 are virtual planes which are defined when the structure of the microneedle 10 is regarded as separate parts, the substrate 11 and the projection 12, or even the substrate 11, the columnar portion 13 and the tapered portion 14. These planes do not appear on the outer surface of the microneedle 10.

Specifically, for example, as shown in FIG. 1, the columnar portion 13 has a cylindrical shape, and the tapered portion 14 has a conical shape. Further, for example, as shown in FIG. 2, the columnar portion 13 has a quadrangular prism shape and the tapered portion 14 has a quadrangular pyramid shape. These examples are not exhaustive, and the columnar portion 13 may have a polygonal prism shape other than the quadrangular prism shape, and the tapered portion 14 may have a polygonal pyramid shape other than the quadrangular pyramid shape. In short, the columnar portion 13 is only required to have a columnar shape with the bottom defined by a straight or curved line, and the tapered portion 14 is only required to have a tapered shape with the bottom which is the same as the bottom of the columnar portion 13.

[Detailed Configuration of Projections]

Figure 3:
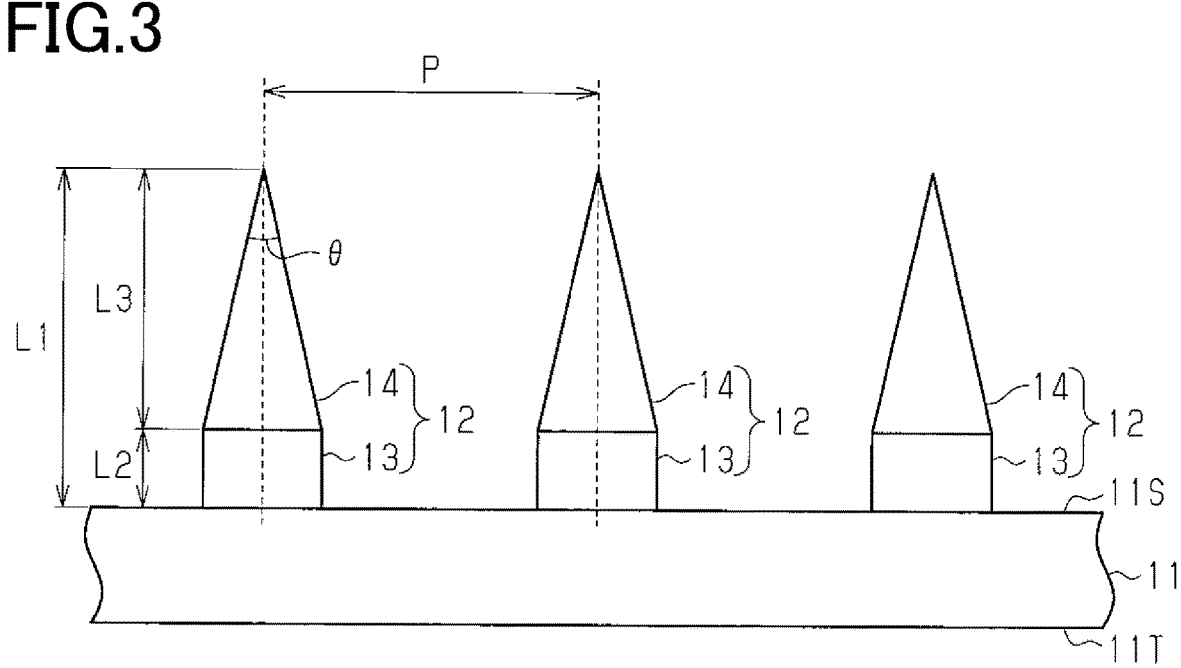
FIG. 3 is a side view which illustrates a side structure of a transdermal administration device of an embodiment.
Figure 4:
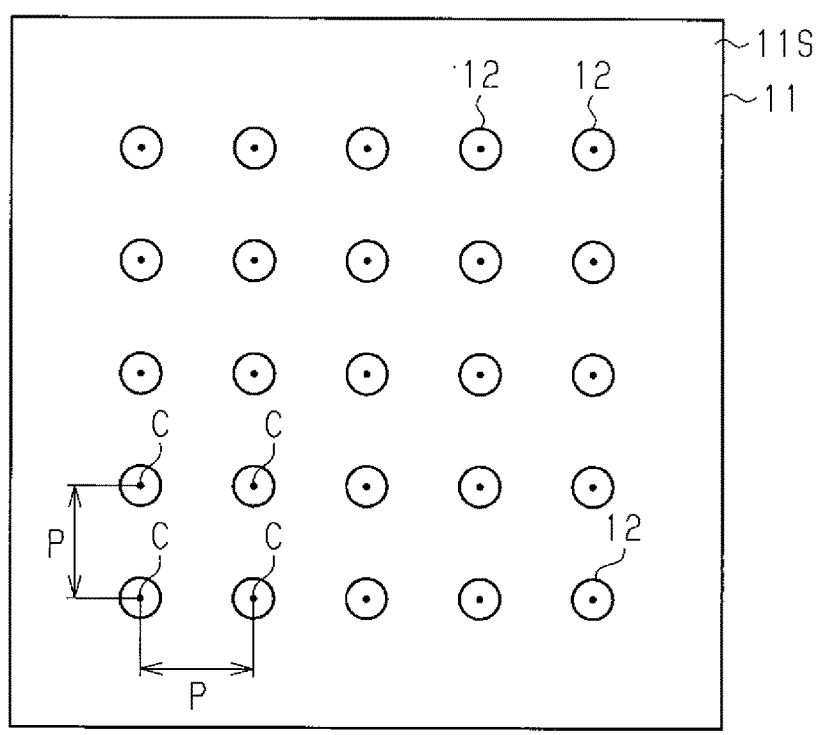
FIG. 4 is a plan view which illustrates a plan structure of a transdermal administration device of an embodiment.
Figure 5:
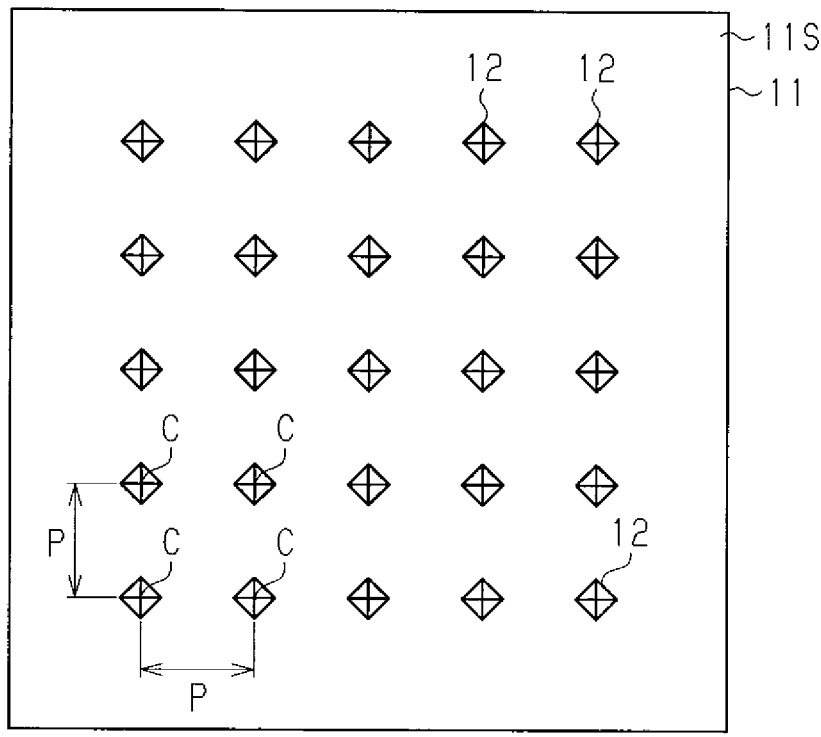
FIG. 5 is a plan view which illustrates another example of a plan structure of a transdermal administration device of an embodiment.

With reference to FIGS. 3 to 5, a detailed configuration of the projection 12 will be described.

As shown in FIG. 3, the projection 12 has a projection length L1, which is a length of the projection 12 from the proximal end to the distal end, that is, from the first surface 11S to the tip of the tapered portion 14 in a direction perpendicular to the first surface 11S of the substrate 11. The columnar portion 13 has a column length L2, which is a length of the columnar portion 13 from the proximal end to the distal end, that is, from the first surface 11S to the upper end of the side surface which is perpendicular to the first surface 11S in a direction perpendicular to the first surface 11S. The tapered portion 14 has a taper length L3, which is a length of the tapered portion 14 from the proximal end to the distal end, that is, from the upper end of the side surface of the columnar portion 13 which is perpendicular to the first surface 11S to the distal end of the projection 12 in a direction perpendicular to the first surface 11S. The projection length L1 is the total length of the column length L2 and the taper length L3.

The projection 12 has a tip angle $\theta$, that is, a tip angle $\theta$ of the tapered portion 14, which is the maximum angle of the apex of the tapered portion 14 as viewed in a direction parallel with the first surface 11S. For example, when the tapered portion 14 has a conical shape, the tip angle $\theta$ of the tapered portion 14 is an apex angle of a triangle having a base, which is a diameter of a circle of the bottom of the tapered portion 14, and an apex, which is an apex of the cone. For example, when the tapered portion 14 has a quadrangular pyramid shape, the tip angle $\theta$ of the tapered portion 14 is an apex angle of a triangle having a base, which is a diagonal of a rectangle of the bottom of the tapered portion 14, and an apex, which is an apex of the quadrangular pyramid.

A pitch P of the projections 12 is a distance between the centers of one projection 12 and another projection 12 closest to each other when viewed in the direction perpendicular to the first surface 11S. In other words, the minimum distance between the centers of the target projection 12 and another projection 12 as viewed in the direction perpendicular to the first surface 11S is the pitch P of the target projection 12.

As shown in FIG. 4, when the columnar portion 13 has a cylindrical shape and the tapered portion 14 has a conical shape, the projection 12 has a center C as viewed in the direction perpendicular to the first surface 11S, which is a center of a circle of the outline of the projection 12 as viewed in this direction, and corresponds to the position of the distal end of the projection 12 as viewed in this direction. That is, the center C of the projection 12 as viewed in the direction perpendicular to the first surface 11S corresponds to the center of the circle of the bottom of the columnar portion 13.

Further, as shown in FIG. 5, when the columnar portion 13 has a quadrangular prism shape and the tapered portion 14 has a quadrangular pyramid shape, the projection 12 has the center C as viewed in the direction perpendicular to the first surface 11S, which is an intersection of diagonals of a rectangle of the outline of the projection 12 as viewed in this direction, and corresponds to the position of the distal end of the projection 12 as viewed in this direction. That is, the center C of the projection 12 as viewed in the direction perpendicular to the first surface 11S corresponds to the center of gravity of the rectangle of the bottom of the columnar portion 13.

In short, the center C of the projection 12 as viewed in the direction perpendicular to the first surface 11S is the center of gravity of the shape of the outline of the projection 12 as viewed in this direction, that is, the center of gravity of the shape of the bottom of the columnar portion 13.

The microneedle 10 of the present embodiment satisfies the following conditions (a) to (c).

(a) The tip angle $\theta$ of the tapered portion 14 is in the range of 10° or more and 30° or less.

(b) The pitch P of the projection 12 is in the range of 50 μm or more and 350 μm or less.

(c) A ratio of the taper length L3 to the projection length L1 is in the range of 0.45 or more and 0.75 or less.

The sharper the apex of the projection 12, the more smoothly the projection 12 punctures the skin. The tip angle $\theta$ less than 30° can sufficiently ensure smooth puncture. Meanwhile, the tip angle $\theta$ of 10° or more can prevent excessive decrease in strength of the projection 12 which is caused by the thinness of the apex.

When a user of the microneedle 10 presses the second surface 11T of the substrate 11 to pierce the projections 12 into the skin, the sparser the arrangement of the plurality of projections 12 on the first surface 11S of the substrate 11, that is, the larger the pitch P of the projections 12, the smaller the number of projections 12 receiving a pressing force applied to the first surface 11S per unit area. As a result, the force applied per projection 12 increases, which may cause the projections 12 to be susceptible to deformation. In particular, as the tip angle $\theta$ decreases in order to improve smoothness of puncture by the projections 12, the strength of the projections 12 decreases. Accordingly, having projections 12 susceptible to deformation due to the arrangement of the projections 12 is problematic.

On the other hand, as the pitch P of the projections 12 decreases and the plurality of projections 12 are more densely arranged, the pressing force is distributed to thereby reduce the force applied per projection 12, which ensures the projections 12 are less easily deformed. However, the degree to which the pitch P can be minimized is limited by the size of the bottom of the projection 12. In the present embodiment, the projection 12 has a shape composed of a columnar body and a tapered body connected thereto. Accordingly, compared with the projection 12 having a configuration in which the entire projection has a tapered shape, that is, the cross-section of the projection in the direction parallel with the first surface 11S of the substrate 11 increases in size toward the proximal end of the projection, the bottom of the projection 12 of the present embodiment can be reduced in size with the same tip angle $\theta$. Therefore, the pitch P of the plurality of projections 12 can be reduced and thus the projections 12 can be densely arranged. That is, the plurality of projections 12 can be densely arranged while having sharp apexes.

When the pitch P of the projections 12 is 350 μm or less, the pressing force is sufficiently distributed, ensuring the projections 12 are not easily deformed. On the other hand, when the pitch P is 50 μm or more, an excessively dense arrangement of the plurality of projections 12, which causes close distance between the projections 12, can be decreased or prevented. Accordingly, smooth puncture into the skin by the projection 12 is not impaired. Moreover, difficulties in production of the plurality of projections 12 can also be decreased or prevented.

Because the surface of the skin is not flat, it is difficult to pierce the plurality of projections 12 into the skin while holding the first surface 11S of the substrate 11 to be parallel with the surface of the skin. Thus, when the projections 12 puncture the skin, the projections 12 undergo not only a force in the direction perpendicular to the first surface 11S but also a force in the direction parallel with the first surface 11S to no small extent. The strength of the projection 12 against the force in the direction parallel with the first surface 11S decreases with an increase in the proportion of the area surrounded by a side surface which extends vertically from the first surface 11S in the projection 12. In contrast, the proportion of the columnar portion 13 in the projection 12 does not become too large if a ratio of the taper length L3 to the projection length L1, that is, a proportion of the tapered portion 14 in the projection 12 in the direction perpendicular to the first surface 11S, is 0.45 or more. Accordingly, the strength of the projection 12 against a force in the direction parallel with the first surface 11S can be prevented from decreasing. On the other hand, when the ratio of the taper length L3 to the projection length L1 is 0.75 or less, an effect by virtue of the shape of the projection 12, which is composed of a columnar body and a tapered body connected thereto, can be sufficiently exhibited.

Thus, with the above conditions (a) to (c) satisfied, the projections 12 can improve both resistance to deformation and smooth puncture into the skin, and thus improve puncture performance of the respective projections 12.

Moreover, the projection length L1 is preferably in the range of 50 μm or more and 800 μm or less. The projection length L1 may be determined according to the depth or volume required for the puncture created by the projection 12.

Further, the plurality of projections 12 may be arranged regularly or irregularly on the first surface 11S of the substrate 11 as far as the pitch P of the projections 12 is in the range of 50 μm or more and 350 μm or less. When the plurality of projections 12 are regularly arranged, the plurality of projections 12 are arrayed, for example, in a matrix or coaxial arrangement.

In the examples illustrated in FIGS. 4 and 5, the plurality of projections 12 are arrayed in matrix with an equal pitch P therebetween. When viewed in the direction perpendicular to the first surface 11S, the respective projections 12 are arrayed with the pitch P, which is the distance between the centers C of the adjacent projections 12 in two directions perpendicular to each other, that is, in the vertical direction and the horizontal direction in the drawing. In other words, when viewed in the direction perpendicular to the first surface 11S, the distance is constant between the centers C of the target projection 12 and all the projections 12 adjacent to the target projection 12 in two directions perpendicular to each other, which are the projections 12 closest to the target projection 12.

According to the above configuration, a pressing force applied to the substrate 11 is equally distributed, preventing variation in puncture performance of the projections 12.

Figure 6:
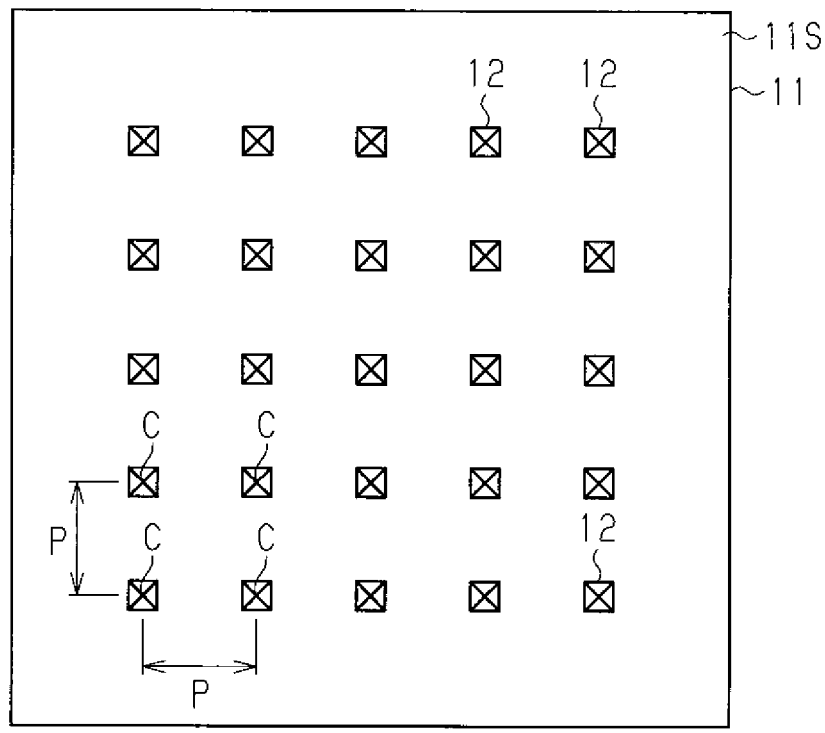
FIG. 6 is a plan view which illustrates another example of a plan structure of a transdermal administration device of an embodiment.

Further, FIG. 5 illustrates a configuration in which the projections 12 are arrayed with the pitch P, which is the distance between the centers C of the adjacent projections 12 in the directions of the diagonals of the rectangle of the outline of the projection 12 as viewed in the direction perpendicular to the first surface 11S. Alternatively, as shown in FIG. 6, the projections 12 may be arrayed with the pitch P, which is the distance between the centers C of the adjacent projections 12 in the directions along the sides of the rectangle of the outline of the projection 12 as viewed in the direction perpendicular to the first surface 11S.

[Production Method of Transdermal Administration Device]

Materials and production methods for the microneedle 10 will be described.

The microneedle 10 is preferably made of a biocompatible material. Examples of the material for forming the microneedle 10 include silicon, metals such as stainless steel, titanium, and manganese, and thermoplastic resins such as medical grade silicone, polylactic acid, polyglycol acid, polycarbonate, and cyclic olefin copolymer. Further, the microneedle 10 may be formed of a material soluble in water contained in the skin, that is, a water-soluble material. The water-soluble material may be a water-soluble polymer or polysaccharide. Examples of the water-soluble polymer include carboxymethyl cellulose (CMC), methylcellulose (MC), hydroxylpropyl cellulose (HPC), hydroxypropyl methylcellulose (HPMC), polyvinyl alcohol (PVA), polyacrylic acid polymer, polyacrylic amide (PAM), polyethylene oxide (PEO), pullulan, alginate, pectin, chitosan, chitosan succinamide, and oligochitosan. Among these materials, chitosan, chitosan succinamide, carboxymethyl cellulose (CMC), hydroxylpropyl cellulose (HPC), and hydroxypropyl methylcellulose (HPMC) can be preferably used because they have high biological safety. Further, examples of the saccharides include trehalose or maltose. The projection 12 made of a water-soluble material dissolves in the skin after it is pierced into the skin.

Further, the microneedle 10 may include a plurality of regions formed of materials different from each other. These regions formed of materials different from each other may have a layered configuration. In other words, the microneedle 10 may be formed of a plurality of layers made of materials different from each other.

Figure 7:
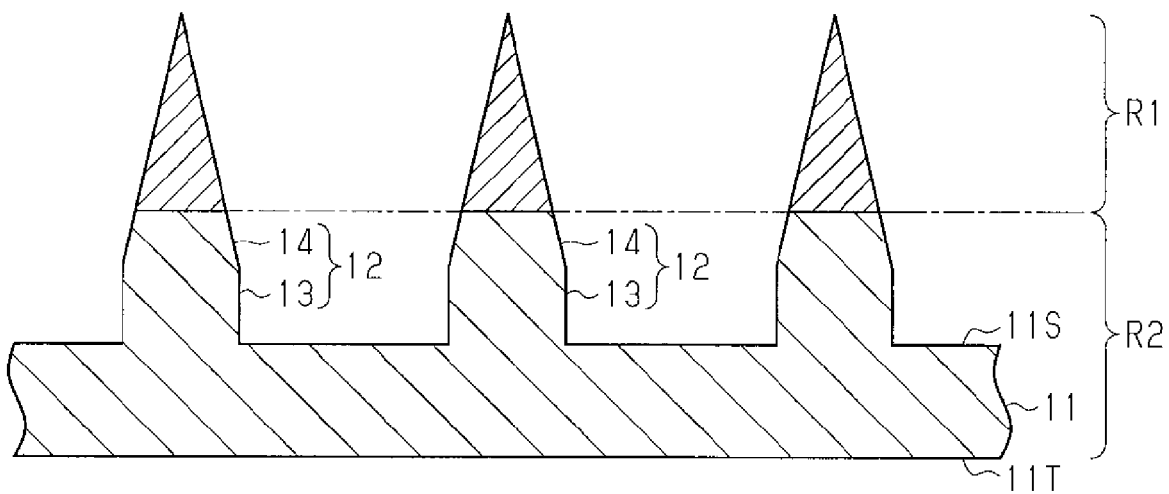
FIG. 7 is a cross-sectional view which illustrates a cross-sectional structure in another example of a transdermal administration device of an embodiment.

FIG. 7 illustrates an example in which a portion of the projection 12 which includes the distal end constitutes a first layer R1 which is made of a first material, and a portion of the projection 12 which includes the proximal end and the substrate 11 constitute a second layer R2 which is made of a second material. The first material and the second material have different compositions, and an interface between the first layer R1 and the second layer R2 extends parallel with the first surface 11S of the substrate 11.

Although FIG. 7 illustrates a configuration in which the interface between the first layer R1 and the second layer R2 is located in the tapered portion 14 of the projection 12, the interface between the first layer R1 and the second layer R2 may be located at the boundary between the tapered portion 14 and the columnar portion 13, in the columnar portion 13, at the boundary between the projection 12 and the substrate 11, or in the substrate 11. Further, the interface between the first layer R1 and the second layer R2 may not be necessarily parallel with the first surface 11S. Further, the microneedle 10 may be formed of three or more layers made of materials different from each other.

A drug to be administered by using the microneedle 10 may be applied on the surface of the projections 12 and delivered into the skin as the projections 12 puncture the skin. Alternatively, when the projections 12 are made of a soluble material as described above, a drug may be contained in the projections 12 and delivered into the skin as the projections 12 dissolve. Alternatively, when the projections 12 have a groove or aperture, a drug may be loaded in the groove or aperture and delivered into the skin as the projections 12 puncture the skin. Further, a liquid drug may be applied on the skin before or after the projections 12 are pierced into the skin so that the drug is delivered into the skin through the holes created by the projections 12. Moreover, a drug may be applied by combinations of these techniques. Further, when the projections 12 may be made of a soluble material, a water-soluble material which constitutes the projections 12 may serve as a drug.

Any kind of drug may be used as long as it works when administered into the skin. A drug may be, for example, pharmacologically active agents or cosmetic compositions, which are appropriately selected depending on the purpose.

Examples of a pharmacologically active agent include vaccines such as influenza vaccine, pain relievers for cancer patients, insulin, biologics, gene therapy agents, injections, oral agents, skin application preparations and the like. In transdermal administration using the microneedle 10, a drug is administered into a hole created in the skin. Therefore, transdermal administration using the microneedle 10 can be applied to not only administration of the pharmacologically active agents used in the conventional transdermal administration, but also administration of pharmacologically active agents that require hypodermic injection. In particular, transdermal administration using the microneedle 10 is suitable for administration of an injection medication such as a vaccine for children because it does not cause pain to a patient during administration. Further, transdermal administration using the microneedle 10 is suitable for administration of an oral medication for children who have difficulty in swallowing an oral medication because it does not require a patient to swallow a drug in administration.

Cosmetic compositions are compositions for use as cosmetics or beauty products. Examples of a cosmetic composition include humectants, colorants, fragrance, and physiologically active agents exhibiting cosmetic effects such as improvement effect on wrinkles, acne, stretch marks or the like, and improvement effect on hair loss or the like. When an aromatic material is used as a cosmetic composition, a fragrance can be imparted to the microneedle 10. Accordingly, the microneedle 10 suitable for use as a beauty product can be obtained.

The configuration of the microneedle 10 of the present embodiment can be preferably applied to a case where a water-soluble polymer among these materials is used as a material for forming the projection 12. Because the projection containing a water-soluble polymer as a main component is susceptible to deformation compared with the projection made of other materials such as metal, the projection often has a difficulty in achieving both resistance to deformation and smooth puncture into the skin. On the other hand, in the microneedle 10 in which the projections 12 have the shape and arrangement according to the present embodiment, the projection 12 can improve both resistance to deformation and smooth puncture into the skin even if the projections 12 are made of a water-soluble polymer.

In addition, the water-soluble polymer used as a material for forming the projections 12 is not limited to those listed above. Further, when a water-soluble polymer is used as a material for forming the projections 12, the projections 12 may contain a drug in addition to the water-soluble polymer, or alternatively, the water-soluble polymer itself may work as a drug. Further, the projections 12 may also include various additives in addition to a water-soluble polymer. The main component of the projection 12 is a component having the highest content in the projection 12, and accounts for, for example, 50 mass % or more of the projection 12.

The microneedle 10 can be produced by using various known techniques according to the materials for forming the microneedle 10. For example, when a resin is used as a material for the microneedle 10, the microneedle 10 can be produced by injection molding, extrusion molding, imprinting, hot embossing, casting, or the like. Further, the microneedle 10 can also be produced by using micromachining techniques such as lithography, wet etching, dry etching, sand blasting, laser processing, micromachining, and the like. Alternatively, the microneedle 10 can be produced by combining a plurality of techniques described above.

Further, the microneedle 10 can also be produced by forming an original plate for the microneedle 10 by using the above techniques, and fabricating an intaglio plate having an inverted shape of projections and recesses of the original plate. The intaglio plate is used for production of the microneedle 10. The intaglio plate is formed by a known shape-transfer technique. The shape-transfer technique includes a method of producing an intaglio plate made of nickel by nickel electroforming, a method of transfer molding using a molten resin, and the like. Accordingly, the intaglio plate having recesses corresponding to the shapes of the projections 12 is produced.

The intaglio plate thus formed is then filled with a material for forming the microneedle 10. For example, when the microneedle 10 is made of a water-soluble polymer, a material solution containing the water-soluble polymer and a drug is prepared. The way of supplying the material solution into the intaglio plate may be appropriately selected from known methods taking into consideration the shape, size, or the like of the intaglio plate. The material solution can be supplied by methods such as spin coating, use of dispenser, casting, and ink jetting. As the material solution filled in the intaglio plate is dried and cured, a product is formed as the microneedle 10, and the product is removed from the intaglio plate to be provided as the microneedle 10.

The microneedle 10 formed by using the intaglio plate is not limited to the microneedle 10 made of a water-soluble polymer. For example, a thermoplastic resin may be filled in the intaglio plate by thermal press or the like to produce the microneedle 10 made of a thermoplastic resin.

EXAMPLES

The aforementioned transdermal administration device will be described by using specific Examples and Comparative Examples.

Example 1

A silicon substrate was processed by micromachining to form an original plate of a microneedle which had 36 projections arranged in 6×6 matrix, each having a shape in which a cone is connected to a cylinder. Subsequently, a nickel film was plated on the surface of the original plate at 500 μm thickness. The original plate was then removed by wet-etching using a potassium hydroxide aqueous solution with a concentration of 30 wt % heated at 90° C. to thereby fabricate an intaglio plate made of nickel having an inverted shape of projections and recesses of the original plate.

Then, hydroxypropyl cellulose was dissolved in water to prepare a hydroxypropyl cellulose aqueous solution with a concentration of 5 wt %. The above intaglio plate was filled with the hydroxypropyl cellulose aqueous solution, and the intaglio plate together with the hydroxypropyl cellulose aqueous solution filled in the intaglio plate was heated by using a hot plate heated at 90° C. to thereby dry and cure the filled product. After the cured product was removed from the intaglio plate, the product was punched out into a circle. Thus, a microneedle of Example 1 made of hydroxypropyl cellulose was obtained.

The microneedle of Example 1 included the projections, each of which was formed of a columnar portion of a cylindrical shape and a tapered portion of a conical shape. Each projection had a projection length L1 of 400 µm, a column length L2 of 100 µm, a taper length L3 of 300 µm, a tip angle θ of 30°, and a pitch P was 300 µm.

Example 2

A microneedle of Example 2 made of hydroxypropyl cellulose was obtained by the same process as that of Example 1 except for the shape of the projections of the original plate.

The microneedle of Example 2 included the projections, each of which was formed of a columnar portion of a cylindrical shape and a tapered portion of a conical shape. Each projection had a projection length L1 of 200 µm, a column length L2 of 50 µm, a taper length L3 of 150 µm, a tip angle θ of 25°, and a pitch P was 100 µm.

Example 3

A microneedle of Example 3 made of hydroxypropyl cellulose was obtained by the same process as that of Example 1 except for the shape of the projections of the original plate.

The microneedle of Example 3 included the projections, each of which was formed of a columnar portion of a cylindrical shape and a tapered portion of a conical shape. Each projection had a projection length L1 of 150 µm, a column length L2 of 50 µm, a taper length L3 of 100 µm, a tip angle θ of 10°, and a pitch P was 70 µm.

Example 4

A microneedle of Example 4 made of hydroxypropyl cellulose was obtained by the same process as that of Example 1 except for the shape of the projections of the original plate.

The microneedle of Example 4 included the projections, each of which was formed of a columnar portion of a cylindrical shape and a tapered portion of a conical shape. Each projection had a projection length L1 of 300 µm, a column length L2 of 150 µm, a taper length L3 of 150 µm, a tip angle θ of 30°, and a pitch P was 200 µm.

Example 5

A microneedle of Example 5 made of hydroxypropyl cellulose was obtained by the same process as that of Example 1 except for the shape of the projections of the original plate.

The microneedle of Example 5 included the projections, each of which was formed of a columnar portion of a cylindrical shape and a tapered portion of a conical shape. Each projection had a projection length L1 of 800 µm, a column length L2 of 200 µm, a taper length L3 of 600 µm, a tip angle θ of 25°, and a pitch P was 350 µm.

Example 6

A microneedle of Example 6 made of hydroxypropyl cellulose was obtained by the same process as that of Example 1 except for the shape of the projections of the original plate.

The microneedle of Example 6 included the projections, each of which was formed of a columnar portion of a cylindrical shape and a tapered portion of a conical shape. Each projection had a projection length L1 of 350 µm, a column length L2 of 100 µm, a taper length L3 of 250 µm, a tip angle θ of 15°, and a pitch P was 200 µm.

Example 7

A microneedle of Example 7 made of hydroxypropyl cellulose was obtained by the same process as that of Example 1 except for the shape of the projections of the original plate.

The microneedle of Example 7 included the projections, each of which was formed of a columnar portion of a cylindrical shape and a tapered portion of a conical shape. Each projection had a projection length L1 of 750 µm, a column length L2 of 200 µm, a taper length L3 of 550 µm, a tip angle θ of 30°, and a pitch P was 300 µm.

Comparative Example 1

A microneedle of Comparative Example 1 made of hydroxypropyl cellulose was obtained by the same process as that of Example 1 except for the shape of the projections of the original plate.

The microneedle of Comparative Example 1 included the projections, each of which was formed of a columnar portion of a cylindrical shape and a tapered portion of a conical shape. Each projection had a projection length L1 of 400 µm, a column length L2 of 100 µm, a taper length L3 of 300 µm, a tip angle θ of 30°, and a pitch P was 600 µm.

Comparative Example 2

A microneedle of Comparative Example 2 made of hydroxypropyl cellulose was obtained by the same process as that of Example 1 except for the shape of the projections of the original plate.

The microneedle of Comparative Example 2 included the projections, each of which was formed of a columnar portion of a cylindrical shape and a tapered portion of a conical shape. Each projection had a projection length L1 of 100 µm, a column length L2 of 50 µm, a taper length L3 of 50 µm, a tip angle θ of 15°, and a pitch P was 40 µm.

Comparative Example 3

A microneedle of Comparative Example 3 made of hydroxypropyl cellulose was obtained by the same process as that of Example 1 except for the shape of the projections of the original plate.

The microneedle of Comparative Example 3 included the projections, each of which was formed of a columnar portion of a cylindrical shape and a tapered portion of a conical shape. Each projection had a projection length L1 of 400 µm, a column length L2 of 100 µm, a taper length L3 of 300 µm, a tip angle θ of 8°, and a pitch P was 300 µm.

Comparative Example 4

A microneedle of Comparative Example 4 made of hydroxypropyl cellulose was obtained by the same process as that of Example 1 except for the shape of the projections of the original plate.

The microneedle of Comparative Example 4 included the projections, each of which was formed of a columnar portion of a cylindrical shape and a tapered portion of a conical shape. Each projection had a projection length L1 of 300 μm, a column length L2 of 150 μm, a taper length L3 of 150 μm, a tip angle θ of 35°, and a pitch P was 300 μm.

Comparative Example 5

A microneedle of Comparative Example 5 made of hydroxypropyl cellulose was obtained by the same process as that of Example 1 except for the shape of the projections of the original plate.

The microneedle of Comparative Example 5 included the projections, each of which was formed of a columnar portion of a cylindrical shape and a tapered portion of a conical shape. Each projection had a projection length L1 of 500 μm, a column length L2 of 350 μm, a taper length L3 of 150 μm, a tip angle θ of 20°, and a pitch P was 300 μm.

<Evaluation of Puncture Performance>
(Degree of Deformation)

For each of Examples 1 to 7 and Comparative Examples 1 to 5, a microneedle was pressed against a swine skin to pierce the projections into the skin. Then, the microneedle was pulled out from the skin. The projections of the microneedle pulled out were microscopically observed to count the number of projections that were bent or broken, that is, the number of projections that exhibited deformation after the use of projections. The degree of deformation was rated as sufficient when the number of deformed projections was 7 or less (marked as ○ in Table 1), and insufficient when the number of deformed projections was 8 or more (marked as x in Table 1).

(Smoothness of Puncture)

For each of Examples 1 to 7 and Comparative Examples 1 to 5, the swine skin was microscopically observed after the microneedle was pulled out to count the number of puncture marks which indicate that the hole with a sufficient depth was formed by the projection. The smoothness of puncture into the skin was rated as sufficient when the number of puncture marks was 30 or more (marked as ○ in Table 1), and insufficient when the number of puncture marks was 29 or less (marked as x in Table 1).

<Results>

For the microneedles of Examples 1 to 7 and Comparative Examples 1 to 5, Table 1 shows the shape of projections, column length L2 and taper length L3, a ratio of taper length L3 to projection length L1 (L3/L2+L3), tip angle θ, and pitch P as well as the evaluation result for puncture performance. The ratio of taper length L3 to projection length L1 was rounded to two decimal places.

TABLE 1

| | Shape | Column length L2 (μm) | Taper length L3 (μm) | L3/ L2 + L3 | Tip angle θ (degree) | Pitch P (μm) | Evaluation of puncture performance | |
|---|---|---|---|---|---|---|---|---|
| | | | | | | | Deformation | Puncture |
| Example 1 | Cylinder + Cone | 100 | 300 | 0.75 | 30 | 300 | ○ | ○ |
| Example 2 | Cylinder + Cone | 50 | 150 | 0.75 | 25 | 100 | ○ | ○ |
| Example 3 | Cylinder + Cone | 50 | 100 | 0.67 | 10 | 70 | ○ | ○ |
| Example 4 | Cylinder + Cone | 150 | 150 | 0.50 | 30 | 200 | ○ | ○ |
| Example 5 | Cylinder + Cone | 200 | 600 | 0.75 | 25 | 350 | ○ | ○ |
| Example 6 | Quadrangular prism + Quadrangular pyramid | 100 | 250 | 0.71 | 15 | 200 | ○ | ○ |
| Example 7 | Quadrangular prism + Quadrangular pyramid | 200 | 550 | 0.73 | 30 | 300 | ○ | ○ |
| Comparative Example 1 | Cylinder + Cone | 100 | 300 | 0.75 | 30 | 600 | x (broken) | ○ |
| Comparative Example 2 | Cylinder + Cone | 50 | 50 | 0.50 | 15 | 40 | ○ | x (puncture failed) |
| Comparative Example 3 | Cylinder + Cone | 100 | 300 | 0.75 | 8 | 300 | x (broken) | x (broken) |
| Comparative Example 4 | Cylinder + Cone | 150 | 150 | 0.50 | 35 | 300 | ○ | x (puncture failed) |
| Comparative Example 5 | Cylinder + Cone | 350 | 150 | 0.30 | 20 | 300 | x (broken) | x (broken) |

As shown in Table 1, in Examples 1 to 7 that satisfy three conditions; (a) the tip angle θ of the tapered portion is 10° or more and 30° or less, (b) the pitch P of the projections is 50 μm or more and 350 μm or less, and (c) a ratio of taper length L3 to projection length L1 is 0.45 or more and 0.75 or less, it was found that the resistance to deformation and the smoothness of puncture into the skin were both good, and thus the projections had high puncture performance. In particular, it was found that the puncture performance of projections was high when the projections were formed of water-soluble polymer.

On the other hand, in Comparative Example 1 having the pitch P of the projections larger than the above condition (b), deformation of the projections such as breakage was observed. This is attributable to the fact that the pressing force applied to a single projection becomes too large due to the increased pitch P. Further, in Comparative Example 2 having the pitch P of the projections smaller than the above condition (b), the number of puncture marks which indicate appropriate puncture of the projections was small. This is attributable to the fact that the projections are too densely arranged and a gap between the adjacent projections are too small.

Further, in Comparative Example 3 having the tip angle θ smaller than the above condition (a), a large number of broken projections was observed. Because a large number of projections was broken, the puncture marks which indicate appropriate puncture of the projections was small. This is attributable to the fact that the projections had reduced strength due to the narrow apex of the projections. Further, in Comparative Example 4 having the tip angle θ larger than the above condition (a), the number of puncture marks which indicate appropriate puncture by the projections was small. This is attributable to the fact that the apexes of projections are not sufficiently sharp to puncture. Further, in Comparative Example 5 having the ratio of taper length L3 smaller than the above condition (c), a large number of broken projections was observed. Because a large number of projections were broken, the puncture marks which indicate appropriate puncture of the projections was small. This is attributable to the fact that the proportion of the columnar portion in the projection was too large and the projections have a reduced strength against a force in the direction parallel to the first surface of the substrate.

Example 8

A microneedle of Example 8 was obtained by the same process as that of Example 1 except for using a different type of water-soluble polymer as a material for forming the projections. That is, chitosan succinamide in place of hydroxypropyl cellulose was dissolved in water to prepare a chitosan succinamide aqueous solution with a concentration of 5 wt %. Then, the intaglio plate used in example 1 was filled with the chitosan succinamide aqueous solution, and the intaglio plate together with the chitosan succinamide aqueous solution filled in the intaglio plate was heated by using a hot plate heated at 90° C. to thereby dry and cure the filled product. After the cured product was removed from the intaglio plate, the product was punched out into a circle. Thus, a microneedle of Example 8 made of chitosan succinamide was obtained.

The microneedle of Example 8 included the projections, each of which was formed of a columnar portion of a cylindrical shape and a tapered portion of a conical shape. Each projection had a projection length L1 of 400 μm, a column length L2 of 100 μm, a taper length L3 of 300 μm, a tip angle θ of 30°, and the pitch P was 300 μm.

Comparative Example 6

A microneedle of Comparative Example 6 made of chitosan succinamide was obtained by the same process as that of Example 8 except for the shape of the projections. In Comparative Example 6, the intaglio plate used in Comparative Example 1 was used.

The microneedle of Comparative Example 6 included the projections, each of which was formed of a columnar portion of a cylindrical shape and a tapered portion of a conical shape. Each projection had a projection length L1 of 400 μm, a column length L2 of 100 μm, a taper length L3 of 300 μm, a tip angle θ of 30°, and a pitch P was 600 μm.

Comparative Example 7

A microneedle of Comparative Example 7 made of chitosan succinamide was obtained by the same process as that of Example 8 except for the shape of the projections. In Comparative Example 7, the intaglio plate used in Comparative Example 2 was used.

The microneedle of Comparative Example 7 included the projections, each of which was formed of a columnar portion of a cylindrical shape and a tapered portion of a conical shape. Each projection had a projection length L1 of 100 μm, a column length L2 of 50 μm, a taper length L3 of 50 μm, a tip angle θ of 15°, and a pitch P was 40 μm.

<Evaluation of Puncture Performance>

For the microneedles of Example 8 and Comparative Examples 6 and 7, the degree of deformation and smoothness of puncture were evaluated in the same manner as Examples 1 to 7 and Comparative Examples 1 to 5.

<Results>

For each of Example 8 and Comparative Examples 6 and 7, Table 2 shows the shape of projections, column length L2 and taper length L3, a ratio of taper length L3 to projection length L1 (L3/L2+L3), tip angle θ, and pitch P as well as the evaluation result for puncture performance.

TABLE 2

|  | Shape | Column length L2 (μm) | Taper length L3 (μm) | L3/ L2 + L3 | Tip angle θ (degree) | Pitch P (μm) | Evaluation of puncture performance | |
|---|---|---|---|---|---|---|---|---|
|  |  |  |  |  |  |  | Deformation | Puncture |
| Example 8 | Cylinder + Cone | 100 | 300 | 0.75 | 30 | 300 | ○ | ○ |
| Comparative Example 6 | Cylinder + Cone | 100 | 300 | 0.75 | 30 | 600 | x (broken) | ○ |
| Comparative Example 7 | Cylinder + Cone | 50 | 50 | 0.50 | 15 | 40 | ○ | x (puncture failed) |

As shown in Table 2, it was implied that the results were not changed even if the projections were made of a different type of water-soluble polymer from that of Examples 1 to 7. That is, in Example 8 which satisfies the above conditions (a) to (c), it was found that the resistance to deformation and the smoothness of puncture into the skin were both good, and thus the projections had high puncture performance. This result implies that the puncture performance of the projections made of a water-soluble polymer was improved regardless of the types of water-soluble polymer as far as the above conditions (a) to (c) are satisfied.

Example 9

A sheet made of a cyclic olefin copolymer (COC) was placed on the intaglio plate used in Example 1, and the COC sheet was heat-melted by using a hot plate. The COC sheet heat-melted was pressed by using a metal plate to fill the recesses of the intaglio plate with COC. Then, the intaglio plate and the COC filled in the recesses were cooled to remove the cured product from the intaglio plate. Thus, a microneedle of Example 9 made of COC was obtained.

The microneedle of Example 9 included the projections, each of which was formed of a columnar portion of a cylindrical shape and a tapered portion of a conical shape. Each projection had a projection length L1 of 400 μm, a column length L2 of 100 μm, a taper length L3 of 300 μm, a tip angle θ of 30°, and a pitch P was 300 μm.

Comparative Example 8

A microneedle of Comparative Example 8 made of COC was obtained by the same process as that of Example 9 except for the shape of the projections. In Comparative Example 8, the intaglio plate used in Comparative Example 1 was used.

The microneedle of Comparative Example 8 included the projections, each of which was formed of a columnar portion of a cylindrical shape and a tapered portion of a conical shape. Each projection had a projection length L1 of 400 μm, a column length L2 of 100 μm, a taper length L3 of 300 μm, a tip angle θ of 30°, and a pitch P was 600 μm.

Comparative Example 9

A microneedle of Comparative Example 9 made of COC was obtained by the same process as that of Example 9 except for the shape of the projections. In Comparative Example 9, the intaglio plate used in Comparative Example 2 was used.

The microneedle of Comparative Example 9 included the projections, each of which was formed of a columnar portion of a cylindrical shape and a tapered portion of a conical shape. Each projection had a projection length L1 of 100 μm, a column length L2 of 50 μm, a taper length L3 of 50 μm, a tip angle θ of 15°, and a pitch P was 40 μm.

<Evaluation of Puncture Performance>

For the microneedles of Example 9 and Comparative Examples 8 and 9, the degree of deformation and smoothness of puncture were evaluated in the same manner as Examples 1 to 7 and Comparative Examples 1 to 5.

<Results>

For each of Example 9 and Comparative Examples 8 and 9, Table 3 shows the shape of projections, column length L2 and taper length L3, a ratio of taper length L3 to projection length L1 (L3/L2+L3), tip angle θ, and pitch P as well as the evaluation result for puncture performance.

TABLE 3

| | Shape | Column length L2 (μm) | Taper length L3 (μm) | L3/ L2 + L3 | Tip angle θ (degree) | Pitch P (μm) | Evaluation of puncture performance | |
|---|---|---|---|---|---|---|---|---|
| | | | | | | | Deformation | Puncture |
| Example 9 | Cylinder + Cone | 100 | 300 | 0.75 | 30 | 300 | ○ | ○ |
| Comparative Example 8 | Cylinder + Cone | 100 | 300 | 0.75 | 30 | 600 | x (broken) | ○ |
| Comparative Example 9 | Cylinder + Cone | 50 | 50 | 0.50 | 15 | 40 | ○ | x (puncture failed) |

As shown in Table 3, it was implied that the results were the same as those of the projections made of water-soluble polymer even if the projections were made of a material other than the water-soluble polymer. That is, in Example 9 which satisfies the above conditions (a) to (c), it was found that the resistance to deformation and the smoothness of puncture into the skin were both good, and thus the projections had high puncture performance. This result implies that the puncture performance of projections can also be improved when the projections are made of a material that can form the projections having higher strength and rigidity than the projections made of a water-soluble polymer.

Example 10

Hydroxypropyl cellulose was dissolved in water to prepare a hydroxypropyl cellulose aqueous solution with a concentration of 5 wt %. Then, the hydroxypropyl cellulose aqueous solution was colored by Evans blue to thereby obtain a first material solution.

Further, chitosan succinamide was dissolved in water to prepare a chitosan succinamide aqueous solution with a concentration of 5 wt % as a second material solution.

After the intaglio plate used in Example 1 was filled with the first material solution, part of the first material solution in the intaglio plate was scraped out by using a squeegee. Then, the first material solution in the intaglio plate was heat-melted by using a hot plate heated at 90° C. to thereby dry and cure the filled product.

Further, the second material solution was poured on the cured first material solution. The second material solution in the intaglio plate was heat-melted by using a hot plate heated at 90° C. to thereby dry and cure the filled product.

After the cured product was removed from the intaglio plate, the product was punched out into a circle. Thus, a microneedle of Example 10 was obtained. The microneedle of Example 10 was formed of two layers made of materials different from each other.

The microneedle of Example 10 included the projections, each of which was formed of a columnar portion of a cylindrical shape and a tapered portion of a conical shape. Each projection had a projection length L1 of 400 μm, a column length L2 of 100 μm, a taper length L3 of 300 μm, a tip angle θ of 30°, and a pitch P was 300 µm. Further, microscopic observation of the respective projections revealed that regions around the distal end of the projections were colored in blue.

For the microneedles of Example 10, the degree of deformation and smoothness of puncture were evaluated in the same manner as Examples 1 to 7 and Comparative Examples 1 to 5. For evaluation of degree of deformation, the number of projections which exhibited deformation after puncture was 7 or less. Further, for evaluation of smoothness of puncture, the number of puncture marks which indicate that the hole with a sufficient depth was formed by the projection was 30 or more. Accordingly, it was found that in Example 10 the resistance to deformation and the smoothness of puncture into the skin were both good, and thus the projections had high puncture performance.

As described above with reference to the Examples and Comparative Examples, the inventors of the present application analyzed how the tip angle θ of the tapered portion 14, the pitch P of the projection 12, the shape of the projection 12, and the ratio of the taper length L3 to the projection length L1 affect the puncture performance of the projections 12, taking into consideration the mutual relations among these elements, and found the conditions under which the projections have improved resistance to deformation and smoothness of puncture.

As described above, the aforementioned embodiment can work to achieve the following effects.

(1) A plurality of projections 12 are each composed of the columnar portion 13 and the tapered portion 14, and the above conditions (a) to (c) are satisfied. According to this configuration, the apexes of the projections 12 are sufficiently sharp to allow smooth puncture into the skin by the projections 12. Because the projections 12 have a shape composed of a columnar body and a tapered body connected thereto, the bottom of the projection 12 is reduced in size compared with the projection 12 having a configuration in which the entire projection has a tapered shape with the same tip angle θ. Therefore, the pitch P of the plurality of the projections 12 can be reduced and thus the projections 12 can be densely arranged. Because a pressing force applied to the substrate 11 is distributed to thereby reduce the force applied to each projection 12, the projections 12 can be prevented from being deformed during puncture while having sharp apexes. Moreover, because the proportion of the columnar portion 13 in the projection 12 does not become too large, the strength of the projection 12 against a force in the direction parallel with the first surface 11S can be prevented from decreasing even if the projections 12 have a shape composed of a columnar body and a tapered body connected thereto. Thus, according to the above configuration, the projections 12 can improve both resistance to deformation and smooth puncture into the skin, and thus improve puncture performance of the respective projections 12.

(2) According to the configuration in which the columnar portion 13 has a cylindrical shape and the tapered portion 14 has a conical shape, or the configuration in which the columnar portion 13 has a quadrangular prism shape and the tapered portion 14 has a quadrangular pyramid shape, the projection 12 having a shape composed of a columnar body and a tapered body connected thereto can be appropriately implemented. Further, among the shapes composed of a columnar body and a tapered body connected thereto, the shapes of the above configurations are simple with a small change in curvature and relatively few corners, which allows for easy production of the projections 12.

(3) When viewed in the direction perpendicular to the first surface 11S of the substrate 11, a plurality of projections 12 are arrayed in matrix with the pitch P, which is the distance between the centers C of the adjacent projections 12 in two directions perpendicular to each other on the first surface 11S. According to this configuration, because the respective projections 12 are regularly arranged with an equal interval, a pressing force applied to the substrate 11 is equally distributed. Accordingly, variation in puncture performance of the respective projections 12 can be reduced.

(4) Because the projection containing a water-soluble polymer as a main component is more susceptible to deformation compared with the projection made of other materials such as metal, a problem that the projection has a difficulty in achieving both resistance to deformation and smooth puncture into the skin tends to appear. According to the microneedle 10 of the above embodiment, in the projections 12 made of a material containing a water-soluble polymer, the projections can improve both resistance to deformation and smooth puncture into the skin, which is highly advantageous.

Modifications

The above embodiment can be implemented with modifications as described below.

In the plurality of projections 12, the tip angle θ, the pitch P, and the ratio of the taper length L3 to the projection length L1 may not be necessarily constant as far as the above conditions (a) to (c) are satisfied for the respective projections 12. Further, the columnar portion 13 and the tapered portion 14 may also have a groove or aperture.

Reference Signs List: 10 . . . Microneedle; 11 . . . Substrate; 11S . . . First surface; 11T . . . Second surface; 12 . . . Projection; 13 . . . Columnar portion; 14 . . . Tapered portion; L1 . . . Projection length; L2 . . . Column length; L3 . . . Taper length; P . . . Pitch; θ . . . Tip angle.

What is claimed is:

1. A transdermal administration device, comprising:
a substrate having a first surface; and
a plurality of projections extending from the first surface, each projection including a columnar portion having a columnar shape extending from the first surface and a tapered portion having a tapered shape extending from a top of the columnar portion, wherein
in each of the plurality of projections,
a maximum angle of an apex of the tapered portion as viewed in a direction parallel with the first surface is in a range of 10° or more and 30° or less,
a ratio of a taper length to a projection length is in a range of 0.45 or more and 0.75 or less, wherein the projection length is a length from a proximal end to a distal end of the projection in a direction perpendicular to the first surface, and the taper length is a length of from a proximal end to a distal end of the tapered portion in a direction perpendicular to the first surface, and
a pitch, which is a distance between a center of one of the projections and a center of another projection closest to the one of the projections, is in a range of 50 µm or more and 350 µm or less, wherein the center of the projection is a center of gravity of a shape of an outline of the projection as viewed in a direction perpendicular to the first surface.

2. The transdermal administration device of claim 1, wherein the columnar portion has a cylindrical shape and the tapered portion has a conical shape.

3. The transdermal administration device of claim 1, wherein the columnar portion has a quadrangular prism shape and the tapered portion has a quadrangular pyramid shape.

4. The transdermal administration device of claim 1, wherein the plurality of projections are arranged in matrix as viewed in a direction perpendicular to the first surface, and the pitch is a distance between the centers of the projections which are adjacent to each other in two directions perpendicular to each other on the first surface.

5. The transdermal administration device of claim 1, wherein the projection is made of a material including a water-soluble polymer.

6. The transdermal administration device of claim 1, wherein each projection of said plurality comprises (a) a first portion which includes the distal end of the projection and (b) a second portion which includes the proximal end of the projection, wherein first portions of each projection of said plurality constitute a first layer that is made of a first material, and second portions of each projection of said plurality portion of the projection and the substrate constitute a second layer that is made of a second material, which is different in composition from the first material.

7. The transdermal administration device of claim 6, wherein the second layer comprises silicon and the first layer comprises a water soluble polymer.

8. The transdermal administration device of claim 7, wherein the water soluble polymer is selected from carboxymethyl cellulose (CMC), methylcellulose (MC), hydroxylpropyl cellulose (HPC), hydroxypropyl methylcellulose (HPMC), polyvinyl alcohol (PVA), polyacrylic acid polymer, polyacrylic amide (PAM), polyethylene oxide (PEO), pullulan, alginate, pectin, chitosan, chitosan succinamide, and oligochitosan.

9. The transdermal administration device of claim 6, wherein the second layer comprises silicon and the first layer comprises hydroxypropyl cellulose, chitosan succinamide or cyclic olefin copolymer.

\* \* \* \* \*